United States Patent [19]
Brown et al.

[11] Patent Number: 5,612,352
[45] Date of Patent: Mar. 18, 1997

[54] HETEROCYCLIC COMPOUNDS

[75] Inventors: George R. Brown, Wilmslow; Peter J. Harrison, deceased, late of Macclesfield, by Alison Harrison, Executrix; Keith B. Mallion, Knutsford, all of England

[73] Assignee: Zeneca Limited, London, United Kingdom

[21] Appl. No.: 162,093

[22] PCT Filed: Apr. 8, 1993

[86] PCT No.: PCT/GB93/00754

§ 371 Date: Jul. 14, 1994

§ 102(e) Date: Jul. 14, 1994

[87] PCT Pub. No.: WO93/21089

PCT Pub. Date: Oct. 28, 1993

[30] Foreign Application Priority Data

Apr. 10, 1992 [GB] United Kingdom ............... 9207962
Apr. 10, 1992 [GB] United Kingdom ............... 9207965

[51] Int. Cl.$^6$ .......................... A61K 31/46; C07D 211/22
[52] U.S. Cl. .......................... 514/305; 546/133; 546/137
[58] Field of Search ................. 514/305; 546/133, 546/137

[56] References Cited

U.S. PATENT DOCUMENTS

| | | | |
|---|---|---|---|
| 3,405,134 | 10/1968 | Judd | 546/137 |
| 3,534,053 | 10/1970 | Sallay et al. | 546/133 |
| 3,586,694 | 6/1971 | Shen et al. | 548/309.4 |
| 3,655,675 | 4/1972 | Carabateas | 546/224 |
| 3,679,690 | 7/1972 | Carabateas | 546/309 |
| 3,725,410 | 4/1973 | Potoski et al. | 544/362 |
| 3,763,168 | 10/1973 | Carabateas | 546/133 |
| 3,857,848 | 12/1974 | Mauvemay et al. | 546/133 |
| 4,038,402 | 7/1977 | Kaminka et al. | 514/305 |
| 4,599,344 | 7/1986 | Morgan | 514/305 |
| 5,135,935 | 8/1992 | Alberts et al. | 514/305 |
| 5,242,914 | 9/1993 | Kawamoto et al. | 514/210 |
| 5,286,864 | 2/1994 | Walther et al. | 546/137 |
| 5,385,912 | 1/1995 | Neuenschwander et al. | 514/305 |

FOREIGN PATENT DOCUMENTS

| | | |
|---|---|---|
| 77130/91 | 11/1991 | Australia . |
| 1014958 | 8/1977 | Canada . |
| 0307142 | 3/1989 | European Pat. Off. . |
| 0316718 | 5/1989 | European Pat. Off. . |
| 0322182 | 6/1989 | European Pat. Off. . |
| 0328200 | 8/1989 | European Pat. Off. . |
| 0330826 | 9/1989 | European Pat. Off. . |
| 0337637 | 10/1989 | European Pat. Off. . |
| 370415 | 5/1990 | European Pat. Off. . |
| 0412797 | 2/1991 | European Pat. Off. . |
| 458214 | 11/1991 | European Pat. Off. . |
| 0497415 | 8/1992 | European Pat. Off. . |
| 2323303 | 12/1973 | Germany . |
| 2502916 | 11/1975 | Germany . |
| 4116582 | 11/1991 | Germany . |
| 1416958 | 12/1975 | United Kingdom . |
| 2169292 | 7/1986 | United Kingdom . |
| 92/15579 | 9/1992 | WIPO . |
| 93/15073 | 8/1993 | WIPO . |
| 93/16048 | 8/1993 | WIPO . |

OTHER PUBLICATIONS

Bondarenko et al, Khim. Farm. Zh. 1978, 12(11), pp. 56–60.
Mikhlina, E.E. et al, Khim. Farm. Zh. 1973, 7(8), pp. 20–24.
Vorob'eva, V. Ya. et al, Khim. Geterotsikl. Soedin. 1983, 3, 381–385.
Warawa et al., Quinuclidine Chemistry.2.$^1$Synthesis and Antiinflammatory Properties of 2–Substituted Benzhydryl-3-quinuclidinols, J. Med. Chem., 17(5), (1974), 497–501.
Sterling et al., Quaternary and Tertiary Quinuclidine Derivatives as Inhibitors of Choline Uptake, J. Pharm. Sciences, 80(8), (1991), 785–789.
Saunders et al, Novel Quinuclidine–Based Ligands for the Muscarinic Cholinergic Receptor, J. Med. Chem. 33(4), (1990), 1128–1137.
Turchin et al, Stereochemistry of Quinuclidines Containing a Substituent with Aryl (Heteroaryl) Nuclei at Position Three, Khimiko–farmatsevticheskii Zhurnal, 1986, vol. 20, pp. 65–72.

(List continued on next page.)

*Primary Examiner*—C. Warren Ivy
*Assistant Examiner*—Garth M. Dahlen
*Attorney, Agent, or Firm*—Cushman Darby & Cushman Intellectual Property Group of Pillsbury Madison & Sutro, LLP

[57] ABSTRACT

Biphenylylquinuclidine derivatives of formula I, Q—Ar$^1$—Ar$^2$, in which Q is of formula Ia or Ib,

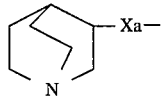

Ia

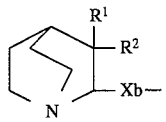

Ib in which $R^1$ and $R^2$ are independently selected from hydrogen, alkyl, halogeno and hydroxy; or $R^1$ and $R^2$ when taken together define an oxo group; Xb is selected from —CH$_2$—, =CH— and —CH(OH); Xa is selected from —CH$_2$—, =CH—, CO, —O—, and —S(O)n (wherein n=0, 1 or 2); Ar$^1$ is a phenylene moiety; Ar$^2$ is phenyl; and wherein one or both of Ar$^1$ and Ar$^2$ is optionally unsubstituted or substituted by one or more substituents independently selected from halogeno, hydroxy, amino, nitro, cyano, carboxy, carbamoyl, alkyl, alkenyl, alkynyl, alkoxy, alkylamino, di-alkylamino, N-carbamoyl, N,N-di-alkylcarbamoyl, alkoxycarbonyl, alkylthio, alkylsulphinyl, alkylsulphonyl, halogeno-alkyl, alkanoyl and alkanoylamino; and their pharmaceutically acceptable salts are inhibitors of squalene synthase and hence useful in treating diseases and medical conditions in which a lowering of cholesterol is desirable. The use of these derivatives in medicine is disclosed tohether with novel compounds, processes for their preparation and pharmaceutical composition containing them.

6 Claims, No Drawings

OTHER PUBLICATIONS

Ricciardi et al., Facile Synthesis of Styrylquinuclidines, Heterocycles,24,(1986), pp. 971–977.

Mikhlina et al, Synthesis and Properties of (3-Quinuclidyl) Diarylcarbinols, Khim. Geterosikl Soedin, 7, 1976, 776–780.

Sekine et al, Effect of Sulfur Containing Purine Nucleosides on Immunological Reaction in Mice, Japan. J. Exp. Med., 1973, vol. 43,5, pp. 369–375.

DeVito et al., Synthesis and Pharmacological Evaluation of Some Novel 13-[N,N]dialkylamino-alkylbenzo[g][2]benzopyrano[4,3-b]indol-5[13H]ones, Med. Chem. Res., 1(1), (1991), pp. 47–51.

Ermakov et al, Application of Mass Spectrometry in Structural and Stereochemical Investigations., Khim. Geterosikl Soedin, 10, (1975), 1376–1383.

Mikhlina et al, Stereochemistry of Benzo[b]Quinuclidines.., Khim. Geterosikl Soedin,6, (1973), pp. 839–843.

Fleet et al., Complex Quinuclidines (1-Azabicyclo[2,2,2] octanes) from Sugars: Synthesis of 1α,3α,4α,5α)-Quinuclidine-3-,5-diol from D-Glucose, J. Chem. Soc. Perkin. Trans., 1(5), (1989), 1067–1068.

Warawa, E.J.; et al. J. Med. Chem. 1974, 17(5), 497–501.

HETEROCYCLIC COMPOUNDS

This application is a 371 of PCT/GB93/00754 filed Apr. 8, 1993.

FIELD OF INVENTION

This invention relates to novel heterocyclic compounds and, more particularly to novel heterocyclic compounds which possess the pharmacologically useful property of inhibiting squalene synthase. The invention also relates to pharmaceutical compositions for use in treating diseases or medical conditions such as hypercholesterolemia and atherosclerosis, as well as other diseases and conditions in which inhibition of squalene synthase is desirable. The invention also relates to processes for the preparation of the novel heterocyclic compounds, and to their use in medicine.

BACKGROUND TO INVENTION

Several different classes of compounds have been reported to possess the capability of being able to lower cholesterol levels in blood plasma. For example agents which inhibit the enzyme HMG CoA reductase, which is essential for the production of cholesterol, have been reported to reduce levels of serum cholesterol. Illustrative of this class of compounds is the HMG CoA reductase inhibitor known as lovastatin which is disclosed in U.S. Pat. No 4,231,938. Other agents which are reported to lower serum cholesterol include those which act by complexing with bile acids in the intestinal system and which are hence termed "bile acid sequestrants". It is believed that many of such agents act by sequestering bile acids within the intestinal tract. This results in a lowering of the levels of bile acid circulating in the enteroheptatic system and promoting replacement of bile acids by synthesis in the liver from cholesterol, which results in an upregulation of the heptatic LDL receptor, and thus in a lowering of circulating blood cholesterol levels.

Squalene synthase (also referred to in the art as squalene synthetase) is a microsomal enzyme which catalyses the first committed step of cholesterol biosynthesis. Two molecules of farnesyl pyrophosphate (FPP) are condensed in the presence of the reduced form of nicotinamide adenine dinucleotide phosphate (NADPH) to form squalene. The inhibition of this committed step to cholesterol should leave unhindered biosynthetic pathways to ubiquinone, dolichol and isopentenyl t-RNA. Elevated cholesterol levels are known to be one of the main risk factors for ischaemic cardiovascular disease. Thus, an agent which inhibits squalene synthase should be useful in treating diseases and medical conditions in which a reduction in the level of cholesterol is desirable, for example hypercholesterolemia and atherosclerosis.

Thus far, the design of squalene synthase inhibitors has concentrated on the preparation of analogues of the substrate farnesyl pyrophosphate (FPP), and hence on compounds which contain phosphorus groups. For example, the preparation of phosphorous-containing squalene synthase inhibitors is reported in published European Patent Application No. 409,181; and the preparation of isoprenoid (phosphinylmethyl)phosphonates as inhibitors of squalene synthase is reported by Biller et al, J. Med. Chem., 1988, 31, 1869.

DISCLOSURE OF INVENTION

The present invention is based on the discovery that certain heterocyclic compounds are inhibitors of squalene synthase, and are hence useful in treating diseases and medical conditions in which inhibition of squalene synthase is desirable.

According to the present invention there is provided a biphenylylquinuclidine derivative of formula I (formula set out hereinafter together with the other chemical formulae referred to herein in Roman numberals), or a pharmaceutically acceptable salt thereof, wherein:

Q is of formula Ia or Ib;

$R^1$ and $R^2$ are independently selected from hydrogen, (1–6C)alkyl, halogeno and hydroxy; or $R^1$ and $R^2$ when taken together define an oxo group;

Xb is selected from —$CH_2$—, =CH— and —CH(OH);

Xa is selected from —$CH_2$—, =CH—, —CH(OH)—, CO, —O—, and —S(O)n (wherein n=0, 1 or 2);

$Ar^1$ is a phenylene moiety;

$Ar^2$ is phenyl; and wherein one or both of $Ar^1$ and $Ar^2$ is optionally unsubstituted or substituted by one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno-(1–6C)alkyl, (1–6C)alkanoyl and (1–6C)alkanoylamino; provided that when Xa is —O—, $Ar^1$ is not unsubstituted 1,4-phenylene and $Ar^2$ is not unsubstituted phenyl;

when one of $R^1$ and $R^2$ is hydroxy, the other of $R^1$ and $R^2$ is not hydroxy or halogeno; and when $R^1$ and $R^2$ together define an oxo group and Xb is =CH—, then $Ar^1$ is not unsubstituted 1,4-phenylene and $Ar^2$ is not unsubstituted phenyl.

It will be appreciated that, depending on the nature of the substituents, certain of the compounds of formula I may possess one or more chiral centres. In such circumstances, it will be appreciated that the compounds of the invention may exist in, and be isolated in, optically active or racemic form. The invention includes any optically active or racemic form of a compound of formula I which possesses the beneficial pharmacological effect of inhibiting squalene synthase. The synthesis of optically active forms may be carried out by standard techniques of organic chemistry well known in the art, for example by, resolution of a racemic form, by synthesis from optically active starting materials or by asymmetric synthesis.

It will also be appreciated that certain compounds of formula I may exist as geometric isomers. It will be understood that the invention includes any such isomers which possess the benefical pharmacological effect of inhibiting squalene synthese.

It is also to be understood that generic terms such as "alkyl" include both the straight chain and branched chain groups such as butyl and tert-butyl. However, when a specific term such as "butyl" is used, it is specific for the straight chain or "normal" butyl group, branched chain isomers such as "t-butyl" being referred to specifically when intended.

A particular value for an alkyl substituent which may be present on $Ar^1$ or $Ar^2$ is, for example, (1–4C)alkyl, such as methyl, ethyl, propyl, isopropyl, butyl, isobutyl or sec-butyl.

A particular value for an alkenyl substituent which may be present on $Ar^1$ or $Ar^2$ is, for example, (2–4C)alkenyl, such as allyl, but-2-enyl or 2-methyl-2-propenyl.

A particular value for an alkynyl substituent which may be present on $Ar^1$ or $Ar^2$ is, for example, (2–4C)alkynyl, such as prop-2-ynyl or but-2-ynyl.

A particular value for an alkoxy substituent which may be present on $Ar^1$ or $Ar^2$ is, for example, (1–4C)alkoxy, such as methoxy, ethoxy, propoxy, isopropoxy or butoxy.

A particular value for an alkylamino substituent which may be present on $Ar^1$ or $Ar^2$ is, for example, (1–4C)alkylamino, such as methylamino, ethylamino, propylamino or butylamino.

A particular value for a di-alkylamino substituent which may be present on $Ar^1$ or $Ar^2$ is, for example, dimethylamino, diethylamino, methylpropylamino or dipropylamino.

A particular value for an alkylcarbamoyl substituent which may be present on $Ar^1$ or $Ar^2$ is, for example, N-methylcarbamoyl, N-ethylcarbamoyl or N-propylcarbamoyl.

A particular value for a di-alkylcarbamoyl substituent which may be present on $Ar^1$ or $Ar^2$ is, for example, N,N-dimethylcarbamoyl or N,N-diethylcarbamoyl.

A particular value for an alkoxycarbonyl substituent which may be present on $Ar^1$ or $Ar^2$ is, for example, methoxycarbonyl, ethoxycarbonyl or propoxycarbonyl.

A particular value for an alkylthio substituent which may be present on $Ar^1$ or $Ar^2$ is, for example, methylthio, ethylthio, propylthio, isopropylthio or butylthio.

A particular value for an alkylsulphinyl substituent which may be present on $Ar^1$ or $Ar^2$ is, for example, methylsulphinyl, ethylsulphinyl, propylsulphinyl, isopropylsulphinyl or butylsulphinyl.

A particular value for an alkylsulphonyl substituent which may be present on $Ar^1$ or $Ar^2$ is, for example, methylsulphonyl, ethylsulphonyl, propylsulphonyl, isopropylsulphonyl or butylsulphonyl.

A particular value for a halogeno substituent which may be present on $Ar^1$ or $Ar^2$ is, for example, fluoro, chloro or bromo.

A particular value for halogenoalkyl substituent which may be present on $Ar^1$ or $Ar^2$ is, for example, one which contains one, two or three halo groups selected from fluoro, chloro and bromo and the alkyl group is selected from methyl, ethyl, propyl, iso-propyl, butyl, isobutyl or sec-butyl. Thus particular values will include fluoromethyl, difluoromethyl and trifluoromethyl.

A particular value for an alkanoyl substituent which may be present on $Ar^1$ or $Ar^2$ is, for example, formyl, acetyl, propionyl or butyryl.

A particular value for an alkanoylamino substituent which may be present on $Ar^1$ or $Ar^2$ is, for example, formamido, acetamido, propionamino, iso-propionamido, butyramino and iso-butyramino.

A particular value for $R^1$ and $R^2$ when alkyl is, for example, (1–4C)alkyl, such as methyl, ethyl, propyl, isopropyl, butyl, iso-butylor sec-butyl.

A particular value for $R^1$ or $R^2$ when halogeno is, for example, fluoro, chloro or bromo.

Particular values for $Ar^1$ include, for example, 1,3-phenylene and 1,4-phenylene.

In one embodiment one or both of $Ar^1$ and $Ar^2$ is optionally unsubstituted or substituted by one or more substituents independently selected from halogeno, hydroxy, nitro, cyano, (1–6C)alkyl, (2–6C)alkenyl, (1–6C)alkoxy, (1–6C)alkylthio, (1–6C)alkylsulphinyl, (1–6C)alkylsulphonyl, halogeno-(1–6C)alkyl and (1–6C)alkanoylamino.

It is generally preferred, for example, that when $Ar^1$ or $Ar^2$ is substituted it bears one, two or three substituents.

It is generally preferred, for example, that $Ar^1$ comprises a 1,4-phenylene moiety (optionally substituted as hereinbefore defined).

It is generally preferred, for example, that when Q is of formula Ib, $R^1$ is hydrogen or (1–6C)alkyl; $R^2$ is hydrogen, hydroxy or halogen; or $R^1$ and $R^2$ together define an oxo group; Xb is —$CH_2$— or —CH(OH)—; is 1,4-phenylene or 1,3-phenylene (especially 1,4-phenylene) $Ar^2$ is phenyl; and $Ar^1$ and $Ar^2$ are optionally substituted as hereinbefore defined.

It is generally preferred, for example, that when Q is of formula Ia, Xa is —S—, =CH—, —$CH_2$, —CO— or —CH(OH)—, $Ar^1$ is 1,4-phenylene; $Ar^2$ is phenyl; and $Ar^1$ and $Ar^2$ are optionally substituted as hereinbefore defined.

In a particular embodiment, Xa is =CH—, —$CH_2$—, —CO or —CH(OH)—; and $R^1$, $R^2$, $Ar^1$ and $Ar^2$ are as defined above.

Specific values include:
for $R^1$, hydrogen and methyl;
for $R^2$, hydrogen, hydroxy and chloro;
or $R^1$ and $R^2$ defined an oxo group;
for Xb —$CH_2$— and —CH(OH)—;
for Xa —S—, =CH—, —$CH_2$—, —CO— and —CH(OH)—
for $Ar^1$ 1,3-phenylene and 1,4-phenylene;
for $Ar^2$ hydroxyphenyl (such as 4-hydroxyphenyl) and halophenyl (such as 4-fluorophenyl).

In one embodiment of the present invention there is provided a compound of formula I, or a pharmaceutically acceptable salt thereof, wherein:
Q is of formula Ib;
$R^1$ and $R^2$ are independently selected from hydrogen, (1–6C)alkyl, halogeno and hydroxy; or $R^1$ and $R^2$ when taken together define an oxo group;
Xb is selected from —$CH_2$—, =CH— and —CH(OH)—;
$Ar^1$ is a 1,4-phenylene moiety; $Ar^2$ is phenyl; and one or both of $Ar^1$ and $Ar^2$ is optionally unsubstituted or substituted by one or more substituents independently selected from halogeno, hydroxy, amino, nitro, cyano, carboxy, carbamoyl, (1–6C)alkyl, (2–6C)alkenyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno-(1–6C)alkyl and (1–6C)alkanoylamino; provided that when one of $R^1$ and $R^2$ is hydroxy, the other of $R^1$ and $R^2$ is not hydroxy or halogeno; and provided that when $R^1$ and $R^2$ together define an oxo group and Xb is =CH—, then $Ar^1$ and $Ar^2$ phenyl rings are not both unsubstituted.

Particular, preferred and specific values are the appropriate values mentioned above.

In a particular embodiment of the present invention, Q is of formula Ib; $R^1$ is hydrogen; $R^2$ is hydrogen, (1–6C)alkyl, halogeno or hydroxy; $Ar^1$ is 1,4-phenylene, $Ar^2$ is phenyl; and one or both of $Ar^1$ and $Ar^2$ is optionally unsubstituted or substituted by one or more substituents independently selected from halogeno, hydroxy, amino, nitro, cyano, carboxy, carbamoyl, (1–6C)alkyl, (2–6C)alkenyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno-(1–6C)alkyl and (1–6C)alkanoylamino.

Particular, preferred and specific values are the appropriate values mentioned above.

In a further embodiment of the present invention Q is of formula Ib; $R^1$ and $R^2$ are independently selected from hydrogen, (1–4C)alkyl, (especially methyl), halogeno (especially chloro), and hydroxy;
or $R^1$ and $R^2$ when taken define from an oxo group.

Xb is —CH₂—, =CH— or —CH(OH)—; Ar¹ is 1,4-phenylene, Ar² is phenyl; and one or both of Ar¹ and Ar² is optionally unsubstituted by one or more substituents independently selected from halogeno, hydroxy, nitro, cyano, (1–6C)alkyl, (2–6C)alkenyl, (1–6C)alkoxy, (1–6C)alkylthio, (1–6C)alkylsulphinyl, (1–6C)alkylsulphonyl, halogeno (1–6C)alkyl and (1–6C)alkanoylamino;

provided that when one of $R^1$ and $R^2$ is hydroxy, the other of $R^1$ and $R^2$ is not hydroxy or halogeno.

Particular, preferred and specific values are the appropriate values mentioned above.

In a further embodiment of the present invention Q is of formula Ib; $R^1$ is hydrogen;

$R^2$ is hydrogen, (1–6C)alkyl, halogeno or hydroxy;

Xb is —CH₂— or =CH—; Ar¹ is 1,4-phenylene; Ar² is phenyl; and one or both of Ar¹ and Ar² is optionally unsubstituted or substituted by one or more substituents independently selected from halogeno, hydroxy, nitro, cyano, (1–6C)alkyl, (2–6C)alkenyl, (1–6C)alkoxy, (1–6C)alkylthio, (1–6C)alkylsulphinyl, (1–6C)alkylsulphonyl, halogeno (1–6C)alkyl and (1–6C)alkanoylamino.

Particular, preferred and specific values are the appropriate value mentioned above.

In a specific embodiment of the present invention Q is of formula Ib;

$R^1$ is hydrogen or (1–4C)alkyl (especially methyl);

$R^2$ is hydrogen, (1–4C)alkyl (such as methyl), halogeno (such as chloro) or hydroxy; or $R^1$ and $R^2$ when taken define an oxo group;

Xb is —CH₂—, =CH— or —CH(OH)—; Ar¹ is 1,4-phenylene, Ar² is phenyl;

and Ar¹ and Ar² are both unsubstituted.

In a further particular embodiment of the present invention there is provided a compound of formula I, or a pharmaceutically acceptable salt thereof, wherein Q is of formula Ia, $X_a$ is selected from —CH₂—, =CH—, —O— and —S(O)n- (wherein n is 0, 1 or 2);

Ar¹ is 1,4-phenylene;

Ar² is phenyl; and one or both Ar¹ and Ar² may be optionally unsubstituted or independently substituted by one or more substituents selected from halogeno, hydroxy, amino, nitro, cyano, carboxy, carbamoyl, (1–6C)alkyl, (2–6C)alkenyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno-(1–6C)alkyl and (1–6C)alkanoylamino; provided that when X is —O—, Ar¹ and Ar² are not both unsubstituted.

Particular and preferred values are the appropriate values mentioned above.

In a particular group of compounds of the above embodiment, $X_a$ is selected from —CH₂—, =CH—, —O— and —S(O)n (wherein n is 0, 1 or 2) and one or both Ar¹ and Ar² may be optionally unsubstituted or independently substituted by one or more substituents selected from halogeno, hydroxy, amino, nitro, cyano, carboxy, carbamoyl, (1–6C)alkyl, (2–6C)alkenyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno-(1–6C)alkyl and (1–6C)alkanoylamino; provided that when X is —O— or —S(O)n- in which n is 0, Ar¹ and Ar² are not unsubstituted or substituted by halogeno, hydroxy, (1–6C)alkyl, amino, (1–6C)alkylamino or di(1–6C)alkylamino.

Particular and preferred values are the appropriate values mentioned above.

In a further embodiment of the present invention $X_a$ is selected from —CH₂— and =CH—; Ar¹ is 1,4-phenylene; Ar² is phenyl, and one or both Ar¹ and Ar² may be optionally unsubstituted or independently substituted by one or more substituents selected from halogeno, hydroxy, amino, nitro, cyano, carboxy, carbamoyl, (1–6C)alkyl, (2–6C)alkenyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno-(1–6C)alkyl and (1–6C)alkanoylamino.

Particular and preferred values are those mentioned above.

In a further embodiment of the present invention Xa is selected from —O— and —S(O)n- (wherein n is 0, 1 or 2); Ar¹ is 1,4-phenylene, Ar² is phenyl; and one or both Ar¹ and Ar² may be optionally unsubstituted or independently substituted by one or more substituents selected from halogeno, hydroxy, amino, nitro, cyano, carboxy, carbamoyl, (1–6C)alkyl, (2–6C)alkenyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno-(1–6C)alkyl and (1–6C)alkanoylamino.

Particular and preferred values are those mentioned above.

Compounds of the invention which are of particular interest include the compounds described in the accompanying Examples (and their pharmaceutically-acceptable salts), and are hence provided as a further feature of the present invention.

A suitable pharmaceutically-acceptable salt of the present invention comprises an acid-addition salt derived from an inorganic or organic acid which provides a pharmaceutically-acceptable anion. Thus, examples of salts of the present invention include acid-addition salts with hydrochloric, hydrobromic, nitric, sulphuric, phosphoric, trifluoroacetic, citric, tartaric, succinic, maleic, fumaric or acetic acid. In addition, suitable pharmaceutically-acceptable salts include [where the compound of formula I is sufficiently acidic, for example where the compound of formula I bears an acidic substituent such as carboxy] those formed with a base which affords a pharmaceutically acceptable cation. Suitable bases include an alkali metal salt (such as a sodium or potassium salt), an alkaline earth metal salt (such as a calcium or magnesium salt), an ammonium salt or a salt with an organic base which affords a physiologically-acceptable cation such as a salt with methylamine, dimethylamine, triethylamine, piperidine or morpholine.

The compounds of the present invention may be obtained by standard procedures of organic chemistry already known to be applicable to the preparation of structurally analogous compounds. Such procedures for the preparation of the compounds of formula I, or pharmaceutically acceptable salts thereof, are provided as a further feature of the present invention and are illustrated by the following preferred processes in which the various generic radicals, for example, $R^1$, $R^2$, Xa, Xb, Ar¹ and Ar² may take any of the meanings hereinbefore defined, and in which Ar¹ and Ar² may optionally be unsubstituted or substituted as hereinbefore defined.

Thus, according to the present invention there is also provided a process for preparing a compound of formula I, or a pharmaceutically-acceptable salt thereof, which process comprises:

(a) For those compounds in which $X_b$ is =CH— and $R^1$ and $R^2$ when taken together form an oxo group, reacting quinuclidin-3-one with an appropriately substituted compound of formula II in the presence of a base.

Suitable bases include, for example, alkali metal hydroxides (such as sodium hydroxide) and alkali metal alkoxides (such as sodium ethoxide). The reaction is generally carried out in a solvent such as an alcohol (eg. ethanol), and at a temperature from ambient temperature to the reflux temperature of the reaction mixture.

(b) For those compounds of formula I in which Q is of formula IV, $X_b$ is =CH$_2$— and $R^1$ and $R^2$ when taken together form an oxo group, selectively reducing a compound of formula I in which $X_b$ is =CH—.

A particularly suitable method of reduction comprises catalytic hydrogenation using a catalyst of, for example, palladium, platinum or nickel and a catalyst in which the metal is supported on an inert carrier such as carbon. A specific example of a suitable catalyst is Pd/C. The reduction is generally carried out in a solvent of, for example, an alcohol such as ethanol.

(c) For those compounds of formula I in which Q is of formula Ib, $R^1$ is hydrogen and $R^2$ is hydroxy, reducing a compound of formula I in which $R^1$ and $R^2$ when taken together define an oxo group.

A suitable way of carrying out the reduction is using a reducing agent which comprises a metal hydride such as sodium borohydride. The reaction is conveniently carried out in a solvent such as an alcohol (eg. methanol).

(d) For those compounds of formula I in which Q is of formula Ib, $R^2$ is halogeno, reacting a compound of formula I in which $R^2$ is hydroxy with a suitable inorganic halide.

Suitable inorganic halides include, for example, SOCl$_2$ or PCl$_5$ (when $R^2$ is chloro), PBr$_3$ (when $R^2$ is bromo) and PI$_3$ (when $R^2$ is iodo). In the case where thionyl chloride is employed, the reaction is generally carried out by refluxing the starting material in thionyl chloride.

(e) For those compounds of formula I in which Q is of formula Ib, $R^1$ is hydroxy and $R^2$ is alkyl, reacting a compound of formula I in which $R^1$ and $R^2$ together define an oxo group with a compound of formula RM in which M is a metal or a derivative thereof and R is an alkyl group.

Suitable values for M include, for example, magnesium and lithium. In the case where M is magnesium it is conveniently present in the form of a derivative of formula —Mg-Hal where Hal is a halogen atom such as iodo or bromo, so that the organometallic compound of formula RM is in the form known as a Grignard Reagent. The reaction is generally carried out in an inert solvent such as dry diethyl ether or tetrahydrofuran, with cooling. For example, when M is a metal such as lithium, the reaction may be carried out at a temperature below 0° C., such as at a temperature between 0° C. and –78° C. When RM is in the form of a Grignard Reagent, the reaction is generally carried out with heating, at for example the reflux temperature of the reaction mixture.

The compounds of formula RM may be prepared from the corresponding alkylhalide of formula R-"hal" wherein "hal" is a halogen atom such as iodo or bromo. The alkyl halide may be reacted with the metal in an inert solvent such as diethyl ether or tetrahydrofuran.

The compounds of formula I in which $R^1$ and $R^2$ together define an oxo group and Xb is —CH(OH) may be prepared by selectively oxidising a compound of formula I in which $R^1$ is hydrogen, $R^2$ is hydroxy and Xb is —CH(OH). In such a reaction the hydroxy group in X is preferably in a protected form.

(f) For those compounds of formula I in which Q is of formula Ib, $R^1$ is hydrogen or alkyl, $R^2$ is hydrogen and $X_b$ is =CH— treating a compound of formula III in which Z is a leaving group with a base.

Suitable values for Z include, for example, halogen such as chloro, bromo or iodo, or a mesyl or tosyl group. Suitable bases include alkali metal hydroxides (such as sodium or potassium hydroxide) and alkali metal alkoxides such as sodium ethoxide.

Compounds of formula III may be prepared from the corresponding compounds of formula I in which $R^2$ is hydroxy. For example compounds of formula III in which Z is chloro may be prepared by reaction of the corresponding compound of formula I in which $R^2$ is hydroxy with thionyl chloride.

(g) For those compounds of formula I in which Q is of formula Ib, $R^1$ and $R^2$ are alkyl, reacting a compound of formula I in which $R^1$ and $R^2$ together define an oxo group with a suitable dialkyl transition metal derivative.

Suitable transition metal derivatives include (alkyl)$_2$TiCl$_2$, and in particular Me$_2$TiCl$_2$; and (alkyl)$_2$CuLi such as Me$_2$CuLi. The reaction is generally carried out in a solvent such as diethyl ether or tetrahydrofuran, with cooling below 0° C.

(h) For those compounds of formula I in which Q is of formula Ib, $R^1$ is hydrogen, $R^2$ is alkyl and X is —CH$_2$— or —CH(OH)—, reducing a compound of formula IV.

Suitable reducing conditions include, catalytic hydrogenation. Suitable reaction conditions are mentioned under (b) above.

The compounds of formula IV may be prepared by, for example, heating a compound of formula I in which Xb is —CH$_2$— or —CH(OH)— (preferably in a protected form), $R^1$ is hydroxy and $R^2$ is alkyl in thionyl chloride and the treating with a base as mentioned in (f) above.

(i) For those compounds of formula I in which Q is of formula Ib, $R^1$ and $R^2$ are halogeno, reacting a compound of formula I in which $R^1$ and $R^2$ together define an oxo group with the appropriate phosphorous halide.

Suitable halides include PCl$_5$, a mixture of PCl$_5$ and PCl$_3$; PB$_3$ and PI$_3$. The reaction ia generally carried out at ambient temperature or with cooling.

(j) For those compounds of formula I in which Q is of formula Ib, $X_b$ is —CH(OH)—, $R^1$ is hydrogen and $R^2$ is hydroxy; reacting quinudlidin-3-one with an appropriately substituted compound of formula II in the presence of a base and subsequently treating with a reducing agent.

A suitable base is, for example, lithium-di-isopropylamide and the reaction is generally carried out in an inert solvent such as tetrahydrofuran. A suitable reducing agent is, for example, a metal hydride such as sodium bis(2-methoxyethoxy)aluminium hydride.

(k) For those compounds of formula I in which Q is of formula Ia, $X_a$ is —S— or —O—, reacting a compound of formula V in which Z is a leaving group with a compound of formula VI in the presence of a base.

Suitable values for Z include, for example, halogeno such as chloro, bromo or iodo, mesyl or tosyl. Suitable bases include, for example, an alkali metal hydroxide (such as sodium hydroxide), an alkaline earth metal carbonate (such as potassium carbonate or an alkali metal hydride (such as sodium hydride). The reaction is generally carried out in a solvent such as dimethylformamide, or dimethylsulphoxide at ambient temperature to the reflux temperature of the reaction mixture.

(l) For those compounds of formula I in which Q is of formula Ia, $X_a$ is —CH$_2$—, reducing a compound in which $X_a$ is =CH—.

The reduction may be carried out, for example, by catalytic hydrogenation using a catalyst such as palladium, platinum or nickel. The reduction is conveniently carried out in a solvent of, for example, an alcohol such as ethanol at ambient temperature.

(m) For those compounds of formula I in which Q is of formula Ia, $X_a$ is S bearing one or two oxygen atoms, oxidising a compound of formula I in which $X_a$ is S.

The compounds of formula I in which X is S may be oxidised using, for example, an appropriate quantity of an oxidising agent such as sodium periodate. Oxidation to compounds in which S bears two oxygen atoms may be carried out using a peracid such as peracetic acid or hydrogen peroxide. The oxidation of sulphur compounds to the corresponding sulphoxides and sulphones is well known in the chemical art.

In some cases some oxidation of the quinuclidine ring may take place to the N-oxide. In such cases the quinuclidine N-oxide moiety may be reduced back to the quinuclidine moiety using agents well known in the art, such as by using sulphur dioxide.

(n) For those compounds of formula I in which Q is of formula Ia, $X_a$ is =CH—, reacting quinudlidin-3-one with a compound of formula VII in the presence of a base.

Suitable bases include alkoxides, such as potassium t-butoxide and the reaction is conveniently carried out in an inert solvent such as tetrahydrofuran.

In the compound of formula VII R, R' and R" are suitable ligands, for example, R, R' and R" may each represent Ph and R may represent =O and R' and R" may represent an alkoxy group such as ethoxy, and W is a counter ion such as chloro.

The compounds of formula VII may be prepared by reaction of a compound of formula VIIa in which W is halogen (such as chloro) with the appropriate phosphorous compound of formula PRR'R".

(p) For those compounds of formula I in which Q is of formula Ia, in which $X_a$ is CO reacting 3-cyanoquinuclidine with a compound of formula VIII in which M is a metal atom or a derivative thereof.

Suitable values for M include, for example, magnesium and lithium. In the case where M is magnesium it is conveniently present in the form of a derivative of formula —MgX where X is a halogen atom such as iodo or bromo, so that the organometallic compound of formula VIII is in the form known as a Grignard Reagent. The reaction is generally carried out in an inert solvent such as dry diethyl ether or tetrahydrofuran. In the case where M is a metal such as lithium the reaction is generally carried out with cooling, for example, at a temperature below 0° C., such as at a temperature between 0° C. and −78° C. Where the compound of formula VIII is in the form of a Grignard Reagent the reaction is generally carried out with heating, for example at the reflux temperature of the reaction mixture.

The compounds of formula VIII may be prepared from a compound of formula VIIIa in which "hal" is a halogen atom, such as iodo or bromo. The compound of formula IIIa may be reacted directly with the metal M. Thus in the case of magnesium, the Grignard Reagent of formula VIII may be prepared by reaction of a compound of formula VIIIa in which "hal" is bromo or iodo with magnesium turnings in an inert solvent such as diethyl ether, as is well known in the art. Where M is lithium, the compound of formula VIII may be prepared by reaction of the compound of formula VIIIa with lithium in an inert solvent such as diethyl ether, or by reaction with an alkyl lithium derivative such as sec-butyl lithium in an inert solvent such as diethyl ether or tetrahydrofuran, as is well known in the art.

(q) For those compounds of formula I in which Q is of formula Ia and $X_a$ is —CH(OH)—, reacting 3-formylquinodidine with a compound of formula VII in which M is a metal atom or a derivative thereof.

Suitable conditions are those mentioned under (p) above.

It will be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein. Suitable protecting groups for hydroxy include, for example, silyl groups such as trimethylsilyl or t-butyldimethylsilyl, tetrahydropyranyl and esterifing groups such as a methyl or ethyl ester; and for amino groups include benzyloxycarbonyl and t-butoxycarbonyl. Carboxy groups may be protected in a reduced form such as in the form of the corresponding protected alcohol, which may be subsequently oxidised to give the carboxy group. The protecting groups may be removed at any convenient stage in the synthesis using conventional techniques well known in the chemical art.

It will also be appreciated that the preferred process for preparing a particular compound of formula I will depend upon the nature of the various radicals. Similarly, the preferred choice of reagent will depend upon the nature of the various radicals present. For example, when it is required to reduce a particular compound the reducing agent will generally be selected to be one which does not interfere with other groupings present.

It will also be appreciated that certain of the various optional substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acylhalide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

When a pharmaceutically-acceptable salt of a compound of the formula I is required, it may be obtained, for example, by reaction of said compound with the appropriate acid (which affords a physiologically acceptable anion), or with the appropriate base (which affords a physiologically acceptable cation), or by any other conventional salt formation procedure.

As mentioned previously, the compounds of the formula I (and their pharmaceutically-acceptable salts) are inhibitors of the enzyme squalene synthase. Thus the compounds of the present invention are capable of inhibiting cholesterol biosynthesis by inhibition of de novo squalene production.

The beneficial pharmacological properties of the compounds of the present invention may be demonstrated using one or more of the following techniques.

(a) Inhibition of Squalene Synthase

In this test, the ability of a compound to prevent the formation of squalene from a radioactive substrate (tritiated farnesyl pyrophosphate) is assessed.

The test compound is incubated at a concentration of 25 micromolar in 200 µl of a buffered solution containing potassium phosphate (50 mM), $MgCl_2$ (4.95 mM), KF (9.9 mM), NADPH (0.9 mM) and rat liver microsomal protein (20 µg). Rat liver microsomes are prepared by the method described in published European Patent Application No. 324,421 and stored in liquid nitrogen prior to assay. Assay vials are kept at 37° C. throughout the incubation.

The reaction is started with the addition of the substrate (1-[$^3$H]-farnesyl pyrophosphate), final concentration 20 µM, and stopped after 15 minutes reaction time with the addition of 50 µl of 4% KOH. The reaction products are separated from unreacted substrate after application to a C-18 octadecyl lccBond column (Analytichem Int product No. 617101). An aqueous fraction is eluted with 250 µl of 0.1M KOH. Squalene is then eluted with 1.0 ml 10% ethylacetate in hexane and radioactivity determined. The difference in radioactivity in the presence and absence of the test compound is used to determine the level of inhibition. If the test compound inhibits at greater than about 70% at 25 micromolar, it is generally re-tested at 25 and 2.5 micromolar. The $IC_{50}$ (concentration which results in a 50% inhibition of squalene production), of the test compound can be determined by testing the compound at several, for example five, concentrations predicted from the two concentration results. The $IC_{50}$ can then be determined from a plot of percentage inhibition against concentration of test compound.

In general, compounds of formula I show significant inhibition in the above test at a concentration in the range of about 0.001 to 25 µM.

By way of illustration of the squalene synthase inhibitory properties of the compound of formula I, the compound described in Example 2 below gave an $IC_{50}$ of $1.2\times10^{-7}$M; and the compound described in Example 10 gave an $IC_{50}$ of $2.1\times10^{-8}$M.

(b) Acute Rat Cholesterol Synthesis Assay

This is an acute in vivo test in the rat to measure de novo hepatic cholesterol synthesis from exogenously administered $^{14}$C-acetate.

Female rats (35–55 g) are housed in reverse lighting conditions (red light from 0200h–1400h) for a period of about 2 weeks prior to test. Animals are allowed free access to chow and drinking water throughout this period. At test, animals should weigh 125–150 g.

Test compounds may be administered by oral gavage, dissolved or suspended in 0.5% polysorbate, or by ip or iv dosing. Control animals receive vehicle alone. After 1 hour the rats are injected ip with 25 µCi [2-$^{14}$C]-acetate (NEN DUPONT. specific activity, 45–60 mCi/mmol NEC-085H, or AMERSHAM specific activity, 50–60 mCi/mmol CFA 14) in a volume of 0.25 ml saline (100 µCi/ml). After a further hour, rats are terminally anaesthetised with halothane and a blood sample obtained from the abdominal vena cava.

1 ml of plasma is lyophilised and then saponified in 2 ml ethanolic KOH (1 part 33% KOH, 9 parts ethanol) at 75° C. for 2 hours. After addition of an equal quantity of water, non-saponifiable lipids are extracted with two 5 ml volumes of hexane. The hexane extracts are evaporated to dryness and the residues dissolved in ethanol to determine choles-terol specific radioactivity. $ED_{50}$ values can be determined in the standard way.

In general, compounds of formula I show activity in the range of about 0.1 to 100 mg/kg.

By way of illustration, the compound described in Example 10 gave in $ED_{50}$ of 46 mg/kg.

No overt toxicity was detected when compounds of the formula I were administered at several multiples of their minimum inhibitory dose or concentration.

As mentioned above, the compounds of the present invention are squalene synthase inhibitors and hence possess the property of inhibiting cholesterol biosynthesis. Thus the compounds of the present invention will be useful in treating diseases or medical conditions in which an inhibition of squalene synthase is desirable, for example those in which a lowering of the level of cholesterol is blood plasma is desirable. In particular, the compounds of the present invention will be useful in treating hypercholesterolemia and/or ischaemic diseases associated with atheromatous vascular degeneration such as atherosclerosis. The compounds of the present invention will also be useful in treating fungal infections.

Thus according to a further feature of the present invention there is provided a method of inhibiting squalene synthase in a warm-blooded animals (such as man) requiring such treatment, which method comprises administering to said animal an effective amount of a compound of formula I, or a pharmaceutically-acceptable salt thereof, wherein:

Q is of formula Ia or Ib;

$R^1$ and $R^2$ are independently selected from hydrogen, (1–6C)alkyl, halogeno and hydroxy; or $R^1$ and $R^2$ when taken together define an oxo group;

Xb is selected from —$CH_2$—, =CH— and —CH(OH);

Xa is selected from —$CH_2$—, =CH—, —CH(OH)—, CO, —O—, and —S(O)n (wherein n=0, 1 or 2);

$Ar^1$ is a phenylene moiety; $Ar^2$ is phenyl; and wherein one or both of $Ar^1$ and $Ar^2$ is optionally unsubstituted or substituted by one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno-(1–6C)alkyl, (1–6C)alkanoyl and (1–6C)alkanoylamino; provided that when one of $R^1$ and $R^2$ is hydroxy, the other of $R^1$ and $R^2$ is not hydroxy or halogeno. In particular, the present invention provides a method of inhibiting cholesterol biosynthesis, and more particularly to a method of treating hypercholesterolemia and atheromatous vascular degeneration (such as atherosclerosis).

Thus the present invention also provides the use of a compound of formula I (as herein defined), or a pharmaceutically-acceptable salt thereof, for the manufacture of a medicament for treating diseases or medical conditions in which a lowering of the level of cholesterol in blood plasma is desirable (such as hypercholesterolemia and atherosclerosis).

When used in the treatment of diseases and medical conditions in which an inhibition of cholesterol biosynthesis is desired, for example in the treatment of hypercholesterolemia or atherosclerosis, it is envisaged that a compound of formula I (or a pharmaceutically acceptable salt thereof) will be administered orally, intravenously, or by some other medically acceptable route so that a dose in the general range of, for example, 0.01 to 50 mg per kg body weight is received. However it will be understood that the precise dose administered will necessarily vary according to the nature and severity of the disease, the age and sex of the patient being treated and the route of administration.

In general, the compounds of formula I (or a pharmaceutically-acceptable salt thereof) will usually be administered in the form of a pharmaceutical composition, that is together with a pharmaceutically acceptable diluent or carrier, and such a composition is provided as a further feature of the present invention.

A pharmaceutical composition of the present invention may be in a variety of dosage forms. For example, it may be in the form of tablets, capsules, solutions or suspensions for oral administration, in the form of a suppository for rectal administration; in the form of a sterile solution or suspension for parenteral administration such as by intravenous or intramuscular injection.

A composition may be obtained by conventional procedures using pharmaceutically acceptable diluents and carriers well known in the art. Tablets and capsules for oral administration may conveniently be formed with a coating, such as an enteric coating (for example, one based on cellulose acetate phthalate), to minimise dissolution of the active ingredient of formula I (or a pharmaceutically-acceptable salt thereof) in the stomach or to mask unpleasant taste.

The compounds of the present invention may, if desired, be administered together with (or sequentially to) one or more other pharmacological agents known to be useful in the treatment of cardiovascular disease, for example, together with agents such as HMG-CoA reductase inhibitors, bile acid sequestrants, other hypocholesterolaemic agents such as fibrates, for example gemfibrozil, and drugs for the treatment of coronary heart disease. As a further example, the compounds of the present invention may, if desired, be administered together with (or sequentially to) an angiotensin converting enzyme (ACE) inhibitor, such as captopril, lisinopril, zofenopril or enalapril.

The compounds of the present invention may also find utility as antifungal agents, and so the present invention also provides a method of treating fungal infections which comprises administration to an a warm blooded animal, such as man, in need of such treatment an effective amount of a compound of formula I, or a pharmaceutically acceptable salt thereof. When used in this way the compounds of the present invention may, in addition to the formulations mentioned above, be adapted for topical administration and such a composition is provided as a further feature of the present invention. Such compositions may be in a variety of forms, for example creams or lotions.

The invention will now be illustrated by the following non-limiting Examples in which, unless otherwise stated:
(i) evaporations were carried out by rotary evaporation in vacuo;
(ii) operations were carried out at room temperature, that is in the range 18°–26° C.;
(iii) yields are given for illustration only and are not necessarily the maximum attainable by diligent process development;
(iv) proton NMR spectra were normally determined at 200 MHz using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet;
(v) all end-products were characterised by microanalysis, NMR and/or mass spectroscopy;
(vi) conventional abbreviations are used for individual radicals and recrystallisation solvents, for example, Me=methyl, Et=ethyl, Pr=Propyl, $Pr^i$=isopropyl, Bu=butyl, $Bu^i$= isobutyl, Ph=phenyl; EtOAc=ethyl acetate, $Et_2O$=ether, MeCN=acetonitrile, MeOH=methanol, EtOH=ethanol, $Pr^iOH$=2-propanol, $H_2O$=water; and
(vii) flash column chromatography or medium pressure liquid chromatography (MPLC) was performed on silica gel [either Fluka Kiesselgel 60 (catalogue no. 60738) obtained from Fluka AG, Buchs, Swtizerland, or Merck Kiesselgel Art. 9385, obtained from E Merck, Darmstadt, Germany].

EXAMPLE 1

2-(4-Phenylbenzylidene)-3-quinuclidinone (2.07 g) in ethyl acetate (50 ml) was hydrogenated at atmospheric pressure for 4 hours over a catalyst of 10% palladium on carbon. The catalyst was removed by filtration and the ethyl acetate evaporated. The crude product was purified by flash chromatography on silica gel using ethyl acetate as eluent to give 2-(4-biphenylmethyl)-3-quinuclidinone as a colourless solid (42% yield), m.p. 97°–98° C., microanalysis, found: C, 81.9; H, 7.0; N, 4.9%; $C_{20}H_{21}NO$ $0.1H_2O$ requires: C, 81.9, H, 7.2; N, 4.8%; NMR ($CDCl_3$) 1.9–2.1 (4H, m), 2.5 (1H, d of t), 2.8–3.0 (3H, m), 3.1–3.3 (3H, m), 3.4–3.5 (1H, m), and 7.3–7.6 (9H, m); m/z 292 (M+H).

The 2-(4-phenylbenzylidene)-3-quinuclidinone used as starting material was obtained by the method of Warawa et al. J. Med Chem, 17, 497, (1974).

EXAMPLE 2

2-(4-Biphenylmethyl)-3-quinuclidinone (650 mg) in dry methanol (13 ml) was treated with sodium borohydride (170 mg) over a period of 30 minutes and the mixture stirred at 20° C. for a further 2 hours. The methanol was evaporated and the crude product was purified by flash chromatography on alumina using hexane/ethyl acetate (1:1) as eluent to give 2-(4-biphenylmethyl)-3-quinuclidinol (35% yield), as a 2:1 mixture of cis:trans isomers, as a colourless solid, m.p. 158°–160° C., microanalysis, found C, 81.4; H, 8.0; N, 4.8%; $C_{20}H_{23}NO$ $0.1H_2O$ requires: C, 81.4; H, 7.9; N, 4.7%; NMR [$(CD_3)_2SO/CD_3COOD$] 1.6–1.8 (2H, m), 2.0–2.3 (3H, m), 2.9–3.6 (6H, m), 3.75–4.1 (2H, m) and 7.3–7.7 (9H, m); m/z 294 (M+H).

The cis:trans mixture of isomers was separated by flash chromatography on silica gel using methanol as eluent to give cis 2-(4-biphenylmethyl)-3-quinuclidinol as a colourless solid, m.p. 172°–174° C., microanalysis found: C, 80.7; H, 7.7; N, 4.9%; $C_{20}H_{23}NO$ 0.25 $H_2O$ requries: C, 80.7; H, 7.9; N, 4.7%; NMR ($CDCl_3$), 1.3–1.4 (1H, m), 1.5–1.7 (3H, m), 1.9–2.0 (2H, m), 2.7–3.0 (4H, m), 3.1–3.3 (3H, m), 3.9 (1H, d of d) and 7.3–7.6 (9H, m); m/z 294 (M+H).

EXAMPLE 3

2-(4-Biphenylmethyl)-3-quinuclidinol (3.0 g) was heated under reflux in thionyl chloride (30 ml) for 30 hours. The thionyl chloride was evaporated and the residue dissolved in 2M sodium hydroxide solution (50 ml). The aqueous mixture was extracted with ethyl acetate, the ethyl acetate phase separated, washed with brine, dried ($Na_2SO_4$) and evaporated.

The crude product was purified by flash chromatography on silica gel using ethyl acetate as eluent to give 2-(4-biphenylmethyl)-3-chloroquinuclidine (10% yield) as a colourless gum, microanalysis, found: C, 68.5; H, 6.7; N, 4.0%; $C_{20}H_{22}ClN$ requires: C, 68.9; H, 6.7; N, 4.0%; NMR [$(CD_3)_2SO$], 1.7–1.9 (2H, m), 1.9–2.2 (3H, m), 2.2–2.3 (1H, m), 3.0–3.5 (5H, m), 3.8–4.0 (1H, m), 4.3–4.4 (1H, m), and 7.3–7.7 (9H, m); m/z 312 (M+H).

(Treatment of the gum with ethereal hydrogen chloride solution gave the hydrogen chloride salt, m.p. 273°–276° C.)

Further elution with ethyl acetate gave 2-(4-biphenylmethyl)-2,3-dehydroquinuclidine (24% yield) as a colourless gum. Treatment of this gum with ethereal hydrogen chloride solution gave the hydrogen chloride salt, 2-(4-biphenylmethyl)-2,3-dehydroquinuclidine hydrogen chloride, m.p. 220°–222° C., microanalysis found: C, 76.2; H, 6.9; N. 4.4%; $C_{20}H_{21}N.HCl. 0.25H_2O$ requires: C, 75.9; H, 6.8; N, 4.4%; NMR [$(CD_3)_2SO$] 1.5–1.7 (2H, m), 1.8–2.0 (2H, m), 2.8–3.0 (3H, m), 3.4–3.5 (2H, m), 3.8 (2H, s), 6.2–6.3 (1H, d) and 7.3–7.7 (9H, m); m/z 276 (M+H).

EXAMPLE 4

2-(4-Biphenylmethyl)-2,3-dehydroquinuclidine hydrochloride (470 mg) in absolute ethanol (45 ml) was hydrogenated at atmospheric pressure for 4 hours over a catalyst of 10% palladium on carbon. The catalyst was removed by filtration and the ethanol evaporated. The residue was crystallised from methanol/ethyl acetate to give 2-(4-biphenylmethyl)quinuclidine hydrochloride (300 mg) as a colourless solid, m.p. 297°–298° C., microanalysis, found: C, 75.7; H, 7.7; N, 4.5%; $C_{20}H_{23}N. HCl 0.25 H_2O$ requires: C, 75.5; H, 7.7; N, 4.4%; NMR [$(CD_3)_2SO$], 1.5–1.6 (1H, m), 1.7–1.9 (4H, m), 1.9–2.1 (1H, m), 2.9–3.1 (1H, m), 3.2–3.4 (7H, m), 3.7–3.8 (1H, m), 7.3–7.5 (5H, m) and 7.6–7.7 (4H, m); m/z 278 (M+H).

EXAMPLE 5

A solution of methylmagnesium iodide in diethyl ether (1.0 ml, 3M) was added dropwise with stirring to a solution of 2-(4-biphenylmethyl)-3-quinuclidinone (580 mg) in dry tetrahydrofuran (20 ml) under an argon atmosphere at −78° C. The mixture was stirred for 5 minutes at −78° C. and then allowed to reach room temperature over a period of 2 hours. 2M Hydrochloric acid (5.0 ml) was then added to the reaction mixture, whilst maintaining the temperature of the reaction mixture below 10° C. The aqueous layer was separated and washed with diethyl ether (2×5 ml) before the addition of an excess of sodium hydroxide solution (density 1.35 g/cm³) to give a pH of 14. The mixture was extracted with ethyl acetate, the ethyl acetate phase separated, dried ($Na_2SO_4$) and evaporated to give 2-(4-biphenylmethyl)-3-methyl-3-quinuclidinol (350 mg) as a colourless solid, m.p. 158°–160° C., microanalysis found: C, 80.8; H, 8.2; N, 4.5%; $C_{21}H_{25}NO 0.25H_2O$ requires: C, 80.9; H, 8.2; N, 4.5%; NMR [$(CD_3)_2SO$] 1.1–1.3 (4H, m), 1.4–1.6 (3H, m), 1.9–2.0 (1H, m), 2.4–2.6 (4H, m), 2.7–2.8 (2H, d of d), 2.9–3.1 (1H, m), 4.1 (1H, s) and 7.2–7.6 (9H, m); m/z 308 (M+H).

EXAMPLE 6

A solution of quinuclidin-3-one (1.55 g) in dry tetrahydrofuran (10 ml) was added dropwise with stirring to a solution of lithium di-isopropylamide (8.33 ml; 1.5M solution in cyclohexane) in dry tetrahydrofuran (50 ml) under an argon atmosphere at −78° C. The mixture was stirred for 10 minutes at −78° C. A solution of 4-biphenylcarboxaldehyde (2.33 g) in dry tetrahydrofuran (20 ml) was then added over a period of 10 minutes. The reaction mixture was stirred at −78° C. for a further 30 minutes. A solution of sodium bis(2-methoxyethoxy)aluminium hydride (14.0 ml; 3.4M solution in toluene) in dry tetrahydrofuran (20 ml) was then added over a period of 20 minutes. The mixture was allowed to reach room temperature over a period of 2 hours, and cold water (20 ml) was then added to the reaction mixture whilst keeping the temperature of the reaction mixture below 10° C. The tetrahydrofuran was removed by decanting, the solid residue washed with diethyl ether (2×50 ml) and the combined ether extracts evaporated to yield crude product. This crude product was purified by flash chromatography on silica gel using ethyl acetate as eluent to give erythro/trans 2-(1-hydroxybiphenyl-4ylmethyl)quinuclidin-3-ol (1.21 g) as a colourless solid, m.p. 159°–160° C., microanalysis found: C, 77.8; H, 7.5; N, 4.4%; $C_{20}H_{23}NO_2$ requires C, 77.6; H, 7.5; N, 4.5%: NMR [$(CD_3)SO/CD_3COOD$], 1.6–1.8 (1H, m), 1.8–1.9 (2H, m), 2.0–2.2 (2H, m). 3.0–3.3 (2H, m), 3.3–3.4 (2H, m), 3.6–3.8 (1H, m), 4.3 (1H, d of d), 5.15 (1H, d) and 7.3–7.7 (9H, m); m/z 310 (M+H).

EXAMPLE 7

A mixture of erythro/trans 2-[1-hydroxy-1-(4'-benzyloxybiphenyl-4-yl)methyl]quinuclidin-3-ol (660 mg) in ethanol (165 ml) was hydrogenated at atmospheric pressure for 4 hours over a catalyst of 10% palladium on carbon. The catalyst was removed by filtration and the filtrate evaporated. The residue was crystallised from methanol to give a mixture of erythro/trans 2-[1-hydroxy-1-(4'-hydroxybiphenyl-4-yl)methyl]quinuclidin-3-ol as a colourless solid (40% yield), m.p. 286°–288° C., microanalysis, found: C, 73.2; H, 7.1; N, 3.9% $C_{20}H_{23}NO_3. 0.1 H_2O$ requires: C, 73.4; H, 7.1; N, 4.3%, NMR ([$CD_3$]$_2SO/CD_3COOD$) 1.6–1.7 (1H, m), 1.85 (1H, s), 2.0 (1H, d), 2.1 (1H, m), 3.0–3.1 (1H, m), 3.1–3.3 (2H, m), 3.3–3.4 (2H, t), 3.6–3.7 (1H, m), 4.2–4.3 (1H, t), 5.1 (1H, d), 6.8–6.9 (2H, d) and 7.4–7.7 (6H, m); m/z 326 (M+H).

The 2-[1-hydroxy-1-(4'-benzyloxybiphenyl-4-yl)methyl] quinudidin-3-ol used as starting material was obtained as follows.

4'-hydroxy 4-biphenylcarboxylic acid (5.0 g) was added to a stirred suspension of sodium hydride (60% w/w dispersion in mineral oil, 2.34 g) in dry dimethylformamide (45 ml) whilst maintaining the temperature of the reaction mixture below 10° C. The reaction mixture was stirred at 10° C. for 20 minutes. A solution of benzyl bromide (8.4 g) in dry dimethylformamide (10 ml) was added over a period of 10 minutes. The reaction mixture was stirred at 70° C. for 2 hours and the mixture was then poured into cold water (900 ml) to precipitate a solid. The solid was collected by filtration, washed with water (3×200 ml) and added to a mixture of 2M aqueous sodium hydroxide solution (100 ml) and ethanol (100 ml). The mixture was stirred at 100° C. for 12 hours. The ethanol was removed by evaporation and the aqueous residue taken to pH 1.0 by the addition of 12M aqueous hydrochloric acid solution to precipitate a solid. The solid was collected by filtration, washed with water (3×100 ml), ethyl acetate (3×100 ml) and dried to give 4'-benzyloxy-4-biphenylcarboxylic acid (100% yield) as a colourless solid, m.p. >300° C.; m/z 304 (M).

Oxalyl chloride (1.72 ml) and dry dimethylformamide (2 drops) were added to a stirred suspension of 4'-benzyloxy-4-biphenylcarboxylic acid (3.04 g) in dry dichloromethane (100 ml). The reaction mixture was stirred for 12 hours at ambient temperature. The mixture was evaporated to dryness. Triphenylphosphine (5.2 g) and bis(triphenylphosphine) copper [I] tetrahydroborate (6.0 g) was added to a solution of the crude product in acetone (150 ml). The mixture was stirred at ambient temperature for 2 hours. The mixture was filtered and the filtrate evaporated. The residue was purified by medium pressure chromatography on silica gel using a mixture of 20% dichloromethane/hexane to remove less polar impurities, followed by ethyl acetate as eluant to give 4'-benzyloxy-4-biphenylcarboxaldehyde as a colourless solid (41% yield), m.p. 122°–123° C., NMR (CDCl$_3$): 5.1 (2H, s), 7.1 (2H, d), 7.4–7.6 (7H, m), 7.7–7.9 (4H, d of d), and 10.0 (1H, s); m/z 289 (M+H).

The 4'-benzyloxy-4-biphenylcarboxaldehyde was converted to 2-[1-hydroxy-1-(4'-benzyloxybiphenyl-4-yl)methyl]quinuclidin-3-ol using the procedure described in Example 6 for the preparation of 2-[1-hydroxy-1-(biphenyl-4-yl)methyl]quinuclidin-3-ol.

There was thus obtained a mixture of erythro/trans 2-[1-hydroxy-1-(4'-benzyloxybiphenyl-4-yl)methyl]quinuclidin-3-ol as a solid (49% yield), m.p. 206°–207° C., microanalysis, found: C, 78.0; H 7.0; N, 3.2%; C$_{27}$H$_{29}$NO$_3$ requires: C, 78.0; H, 7.0; N, 3.4%; NMR ([CD$_3$]$_2$SO/CD$_3$COOD): 1.6–1.7 (1H, m), 1.8–1.9 (1H, m), 2.1–2.3 (2H, m), 3.0–3.1 (2H, m), 3.2 (1H, m), 3.4 (1H, t), 3.5–3.7 (1H, m), 3.7–3.8 (1H, t), 4.3 (1H, d of d), 5.1 (1H, d), 5.2 (2H, s), 7.1 (2H, d of d) and 7.3–7.7 (11H, m); m/z 416 (M+H).

EXAMPLE 8

A solution of 2-[4-(4-fluorophenyl)benzylidene]quinuclidin-3-one (1.3 g) in ethyl acetate (40 ml) was hydrogenated at atmospheric pressure for 4 hours over a catalyst of 10% palladium on carbon. The catalyst was removed by filtration and the filtrate evaporated. The residue was purified by medium pressure chromatography on silica gel using ethyl acetate as eluant to give 2-[4-(4-fluorophenyl)benzyl]quinuclidin-3-one as a colourless solid (38% yield), m.p. 122°–123° C., microanalysis, found: C, 77.5; H, 6.5; N, 4.4% C$_{20}$H$_{20}$FNO requires: C, 77.6; H, 6.5; N, 4.5%; NMR (CDCl$_3$): 1.9–2.1 (4H, m), 2.5 (1H, m), 2.8–3.0 (3H, m), 3.1–3.3 (3H, m), 3.4 (1H, d of d), 7.1 (2H, m), 7.3–7.4 (2H, d) and 7.4–7.6 (4H, m); m/z 310 (M+H).

Further elution with methanol gave a colourless solid which was crystallised from ethyl acetate to give trans 2-[4-(4-fluorophenyl)benzyl]quinuclidin-3-ol (15% yield), m.p. 79°–181° C., microanalysis, found: C, 76.8; H, 7.0; N, 4.4%; C$_{20}$H$_{22}$FNO requires: C, 77.1; H, 7.1; N, 4.5%; NMR (CDCl$_3$): 1.2–1.4 (2H, m), 1.4–1.7 (2H, m); 1.8–2.0 (2H, m), 2.6–3.0 (7H, m), 3.6 (1H, s), 7.1 (2H, m), 7.3–7.4 (2H, d) and 7.4–7.6 (4H, m); m/z 312 (M+H).

Further elution with methanol gave a colourless solid which was crystallised from ethyl acetate to give cis 2-[4-(4-fluorophenyl)benzyl]quinuclidin-3-ol (8% yield), m.p. 180°–182° C., microanalysis, found: C, 77.3; H, 7.1; N, 4.3%; C$_{20}$H$_{22}$FNO requires: C, 77.1; H, 7.1; N, 4.5%; NMR (CDCl$_3$): 1.2–1.4 (2H, m), 1.4–1.7 (2H, m), 1.8–2.0 (2H, m), 2.6–3.0 (4H, m), 3.1–3.3 (3H, m), 3.9 (1H, m), 7.1 (2H, m), 7.4 (2H, d) and 7.4–7.6 (4H, m); m/z 312 (M+H).

The 2-[4-(4-fluorophenyl)benzylidene]quinuclidin-3-one used as starting material was obtained by reaction of quinuclidin-3-one with 4'-fluoro-4-biphenylcarboxaldehyde using the method of Warawa et al. J. Med. Chem. 17, (1974), 497.

The 4'-fluorobiphenyl-4-carboxaldehyde was obtained as follows.

A 1.3M solution of sec-butyl lithium in cyclohexane (6.6 ml) was added to a stirred solution of 4'-fluoro-4-bromobiphenyl (1.76 g) in tetrahydrofuran (35 ml) at a temperature below −75° C. and under an atmosphere of argon. The reaction mixture was stirred at −75° C. for 15 minutes. A solution of dry dimethylformamide (1.74 ml) in dry tetrahydrofuran (3.5 ml) was added to the reaction mixture whilst maintaining the temperature below −75° C. and the reaction mixture was then stirred at −75° C. for a further 30 minutes. The mixture was then allowed to warm to ambient temperature over a period of 2 hours and was then poured into saturated ammonium chloride solution (35 ml). The mixture was extracted with diethyl ether (3×35 ml), the diethyl ether extracts combined, washed with saturated brine (50 ml), dried (MgSO$_4$) and evaporated. The residue was purified by medium pressure chromatography on silica gel using a mixture of 5% ethyl acetate/hexane as eluant to give 4'-fluoro 4-biphenylcarboxaldehyde as a colourless oil (33% yield), microanalysis, found: C, 75.1; H, 4.4%; C$_{13}$H$_9$FO. 0.5H$_2$O requires: C, 75.0; H, 4.8%; NMR (CDCl$_3$): 7.2 (2H, m), 7.6 (6H, m), 7.9 (2H, d) and 10.0 (1H, s), m/z 201 (M+H).

EXAMPLE 9

In a similar manner to that described in Example 8, but using 2-(3-phenylbenzylidine)quinuclidin-3-one as starting material (in place of 2-[4-(4-fluorophenyl)benzylidene]quinuclidin-3-one) there was obtained 2-(3-phenylbenzyl)quinuclidin-3-one as a colourless oil (37% yield), NMR (CDCl$_3$): 1.8–2.0 (4H, m), 2.4 (1H, d of t), 2.7–2.9 (3H, m), 3.0–3.4 (4H, m), and 7.2–7.6 (9H, m).

Also obtained as a colourless solid was a mixture of cis/trans 2-(3-phenylbenzyl)quinuclidin-3-ol (17% yield), m.p. 98°–101° C., NMR (CDCl$_3$): 1.6–2.0, (4H, m), 2.7–3.0 (7H, m), 3.2–3.3 (2H, m) and 7.3–7.6 (9H, m); m/z 294 (M+H).

The 2-(3-phenylbenzylidine)quinudidine-3-one used as starting material was obtained by reaction of 3-biphenylcarboxaldehyde with quinudidine-3-one using the method of Warawa et al., J. Med. Chem., 17, (1974), 497.

The 3-biphenylcarboxyaldehyde was obtained in a similar manner to that described in Example 8 for 4'-fluorobiphenyl-4-carboxyaldehyde using 3-bromobiphenyl as starting material (in place of 4'-fluoro-4-bromobiphenyl) to give 3-biphenylcarboxaldehyde as a colourless oil (1.2% yield) which was used without further characterisation.

EXAMPLE 10

Sodium hydride (0.2 g of a 60% oil dispersion) was added to a stirred solution of 4-mercaptobiphenyl (0.5 g) in dry dimethylformamide (5 ml) under an atmosphere of argon. The reaction mixture was stirred for 30 minutes. 3-Chloroquinuclidine hydrogen chloride (554 mg) was then added and the reaction mixture heated at reflux under an argon atmosphere for 16 hours. The reaction mixture was evaporated to dryness, the residue dissolved in water and extracted with ethyl acetate. The ethyl acetate extract was washed with a saturated solution of sodium hydrogen carbonate, dried (MgSO$_4$) and evaporated. The residue was purified by flash chromatography on silica gel using an eluent of ethyl acetate/methanol/ammonia, density 0.88 g/cm$^3$ (90:8:2) to give 3-(4-biphenylthio)quinuclidine as a solid (305 mg, 38% yield), m.p. 72°–77° C.; microanalysis, found: C, 76.8; H, 7.2; N, 4.74%; C$_{19}$H$_{21}$NS requires: C, 77.2; H, 7.2; N, 4.8%; NMR (CDCl$_3$): 1.4–1.85 (3H, m), 1.9–2.0 (1H, q), 2.0–2.2 (1H, m), 2.7–3.1 (5H, m) and 7.3–7.6 (9H, m); m/Z 296 (M+H)$^+$.

EXAMPLE 11

A solution of diethyl (4-biphenylmethyl)phosphonate (2.14 g, ex Lancaster Synthesis) in dry tetrahydrofuran (40 ml) was added to a stirred solution of potassium tert-butoxide (790 mg) in dry tetrahydrofuran (40 ml) under an atmosphere of argon. The reaction mixture was stirred under an argon atmosphere for 10 minutes. The reaction mixture was then cooled to 0° C. and a solution of quinuclidin-3-one (800 mg) in dry tetrahydrofuran (30 ml) was added over a period of 10 minutes whilst maintaining the temperature of the reaction mixture at 0° C. The reaction mixture was stirred for a further period of 16 hours, during which period the reaction mixture was allowed to warm to ambient temperature. Water was added to the reaction mixture, and the aqueous and ether phases separated. The aqueous phase was extracted with dichloromethane and the dichloromethane and ether extracts were combined, dried ($MgSO_4$) and evaporated. The residue was purified by flash chromatography on silica gel using ethyl acetate/methanol (1:1) as eluent to give Z-3-(4-phenylbenzylidene)quinuclidine (628 mg, 36% yield), as a solid, m.p. 114°–118° C.; microanalysis, found: C, 85.9; H, 7.7; N, 5.1%; $C_{20}H_{21}N$ $0.25H_2O$ requires C, 85.9; H, 7.7; N, 5.0%; NMR ($CDCl_3$): 1.7–1.9 (4H, m), 2.5–2.6 (1H, m), 2.8–3.1 (4H, m), 3.85–3.95 (2H, d), 6.2–6.3 (1H, t), 7.2–7.5 (5H, m) and 7.5–7.65 (4H, m); m/Z 276 $(M+H)^+$; and E-3-(4-phenylbenzylidene)quinuclidine (280 mg, 16% yield), as a solid, m.p. 107° C.; microanalysis, found: C, 85.8; H, 7.7; N, 5.1%; $C_{20}H_{21}N$ $0.25H_2O$ requires: C, 85.9; H, 7.7; N, 5.0%; NMR ($CDCl_3$): 1.7–1.85 (4H, m), 2.9–3.0 (4H, m), 3.05–3.15 (1H, m), 3.6 (2H, br), 6.27 (1H, br) and 7.2–7.6 (9H, m); m/Z 276 $(M+H)^+$.

EXAMPLE 12

Ammonium formate (401 mg) was added to a solution of E/Z 3-(4-phenylbenzylidene)quinuclidine (350 mg) in methanol (16 ml), followed by 10% Pd/C (60 mg) and the resulting reaction mixture stirred at 50°–60° C. under an atmosphere of argon for 30 minutes. The catalyst was removed by filtration and the filtrate evaporated. The residue was purified by flash chromatography on silica gel using an eluent of ethyl acetate/methanol/ammonia, density 0.88 g/cm³ (85:10:5) to give 3-(4-biphenylmethyl)quinuclidine as a gum. This was dissolved in a solution of hydrogen chloride in ethanol and evaporated to give a residue which was crystallised from ethyl acetate to give 3-(4-biphenylmethyl)quinuclidine hydrogen chloride (290 mg, 82% yield) as a solid, m.p. 283°–287° C. (with charring); microanalysis, found: C, 75.7; H, 7.6; N, 4.4%; $C_{20}H_{23}N$. $HCl.0.2H_2O$ requires: C, 75.7; H, 7.6; N, 4.4%; NMR[$(CD_3)_2SO$]: 1.6–1.9 (4H, m), 2.0–2.2 (1H, m), 2.2–2.4 (1H, m), 2.7–2.9 (3H, m), 3.0–3.4 (5H, m), 7.3–7.5 (5H, m), 7.5–7.7 (4H, m), 10.2–10.4 (1H, s); m/Z 278 $(M+H)^+$.

EXAMPLE 13

A solution of sec-butyl lithium in hexane (1.1M, 67.38 ml) was added to a solution of 4-bromobiphenyl (14.38 g) in dry tetrahydrofuran (128 ml) over a period of 1.5 hours under an atmosphere of argon at −78° C. The reaction mixture was stirred for 30 minutes at −78° C. A solution of 3-cyanoquinuclidine (5.6 g) in dry tetrahydrofuran was added to the reaction mixture whilst maintaining the temperature at −78° C. The reaction mixture was stirred for a further period of 16 hours during which period the reaction mixture was allowed to warm to ambient temperature. 2M aqueous hydrogen chloride solution (50 ml) was added to the reaction mixture and the mixture was stirred for 1 hour. The aqueous phase was separated, washed with diethyl ether, basified with dilute aqueous sodium hydroxide solution and extracted with ethyl acetate. The ethyl acetate extract was dried ($MgSO_4$) and evaporated to give a residue which was purified by flash column chromatography on silica gel using a 95:5 (v/v) mixture of methanol/ammonia (density 0.88 g/cm³) as eluant. The residue was dissolved in ethanol and acidified with a saturated solution of ethanolic hydrogen chloride. The mixture was evaporated to dryness and hexane was added to give 3-(4-phenylbenzoyl)quinuclidine hydrogen chloride as a solid (970 mg), m.p. 255.6° C.; microanalysis, found: C, 71.4; H, 6.7; N, 4.4; Cl, 9.8%; $C_{20}H_{21}NO$. HCl ½ $H_2O$. requires: C, 71.34; H, 6.8; N, 4.2; Cl, 10.5%; NMR ($CDCl_3$): 1.7–1.85 (2H, m), 2.0–2.2 (2H, m), 2.2–2.45 (1H, m), 2.45–2.6 (1H, m), 3.2–3.5 (3H, m), 3.5–3.7 (2H, m), 3.9–4.2 (2H, m), 7.35–7.55 (3H, m), 7.55–7.65 (2H, m), 7.65–7.75 (2H, d), 8.0–8.1 (2H, d) and 12.26 (1H, s).

The 3-cyanoquinuclidine used as starting material was prepared as follows.

A solution of potassium tert-butoxide (18.27 ml) in 1:1 (v/v) mixture of dimethoxyethane and ethanol (100 ml) was added slowly to a stirred mixture of 3-quinuclidinone (8.14 g), tosylmethylisocyanate (16.53 g) in dry ethanol (6.5 ml), and dry dimethoxyethane (228 ml) under an atmosphere of argon whilst maintaining the temperature below 10° C. The reaction mixture was allowed to warm to ambient temperature and stirred at this temperature for 30 minutes. The reaction mixture was then stirred at 40° C. for 3 hours. The reaction mixture was cooled, filtered and the filtrate evaporated. The residue was purified by flash column chromatography on alumina (Brockmann Grade I) using a 2:98 (v/v) mixture of methanol/ethyl acetate as eluant to give 3-cyanoquinuclidine (6.6 g), microanalysis, found: C, 67.6; H, 8.5; N, 18.7%; $C_8H_{12}N_2$ requires: C, 70.6; H, 8.8; N, 20.6%; NMR ($CDCl_3$): 1.4–1.7 (3H, m), 1.85–2.0 (1H, m) 2.0–2.1 (1H, m) and 2.6–3.4 (7H, m); m/z 137 (M+H).

EXAMPLE 14

A solution of sec-butyl lithium in cyclohexane (1.3M, 14.87 ml) was added to a solution of 4-bromobiphenyl (4.29 g) in dry tetrahydrofuran (35 ml) under an atmosphere of argon at −78° C. The reaction mixture was stirred at −70° C. for 30 minutes. A solution of freshly prepared 3-quinuclidine carboxaldehyde (2.56 g) in dry tetrahydrofuran was added to the reaction mixture whilst maintaining the temperature at −70° C. The reaction mixture was allowed to warm slowly to ambient temperature and was then stirred for 16 hours under an atmosphere of argon. The reaction mixture was evaporated and the residue was purified by flash column chromatography on silica gel (Merck Art 9385) using a 90:8:2 (v/v) mixture of ethyl acetate/methanol/ammonia (density 0.88 g/cm³) as eluant to give, after crystallisation from ethyl acetate, the diastereomer, (3RS)-3-[(1RS)-1-hydroxybiphenyl-4ylmethyl]quinuclidine as a solid (184 mg), m.p. 182.4° C., microanalysis, found: C, 79.8; H, 7.7; N, 4.5%; $C_{20}H_{23}NO$ $0.4H_2O$ requires: C, 79.95; H, 7.93; N, 4.66%; NMR ([$CD_3$]$_2SO$): 1.2–1.7 (3H, m), 1.75–1.95 (2H, m), 2.1–2.2 (2H, m), 2.25–2.45 (1H, m), 2.55–2.8 (4H, m), 4.3–4.45 (1H, m), 5.1–5.2 (1H, d), 7.3–7.5 (5H, m) and 7.55–7.7 (4H, m); m/z 294 (M+H).

Further elution gave, after crystallisation from ethyl acetate, the diastereomer (3SR)-3-[(1RS)-1-hydroxybiphenyl-4ylmethyl]quinuclidine as a solid (170 mg), m.p. 214.3°

C., microanalysis, found: C, 78.8; H, 7.6; N, 4.4%; $C_{20}H_{23}NO$ 0.65$H_2O$ requires: C, 78.8; H, 7.98; N, 4.59%; NMR ([CD]$_3$SO): 1.1–1.5 (4H, m), 1.65–1.9 (2H, m), 2.6–2.9 (5H, m), 2.9–3.1 (1H, m), 4.4–4.5 (1H, m), 5.1–5.2 (1H, d), 7.3–7.5 (5H, m) and 7.55–7.7 (4H, m); m/z 294 (M+H).

The quinuclidine-3-carboxaldehyde used as starting material was prepared by the method described in Heterocycles, 24, 971–977, (1986).

EXAMPLE 15

Illustrative pharmaceutical dosage forms suitable for presenting the compounds of the invention for therapeutic or prophylactic use include the following tablet and capsule formulations, which may be obtained by conventional procedures well known in the art of pharmacy and are suitable for therapeutic or prophylactic use in humans:

| (a) Tablet I | mg/tablet |
|---|---|
| Compound Z* | 1.0 |
| Lactose Ph. Eur. | 93.25 |
| Croscarmellose sodium | 4.0 |
| Maize starch paste (5% w/v aqueous paste) | 0.75 |
| Magnesium stearate | 1.0 |
| (b) Tablet II | mg/tablet |
| Compound Z* | 50 |
| Lactose Ph. Eur | 223.75 |
| Croscarmellose sodium | 6.0 |
| Maize starch | 15.0 |
| Polyvinylpyrrolidone (5% w/v aqueous paste) | 2.25 |
| Magnesium stearate | 3.0 |
| (c) Tablet III | mg/tablet |
| Compound Z* | 100 |
| Lactose Ph. Eur. | 182.75 |
| Croscarmellose sodium | 12.0 |
| Maize starch paste (5% w/v aqueous paste) | 2.25 |
| Magnesium stearate | 3.0 |
| (d) Capsule | mg/capsule |
| Compound Z* | 10 |
| Lactose Ph. Eur. | 488.5 |
| Magnesium stearate | 1.5 |

Note
*The active ingredient Compound Z is a compound of formula I, or a salt thereof, for example a compound of formula I described in any of the preceding Examples.

The tablet compostions (a)–(c) may be enteric coated by conventional means, for example, with cellulose acetate phthalate.

CHEMICAL FORMULAE

Q—Ar$^1$—Ar$^2$  I

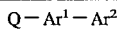  Ia

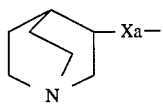  Ib

Ar$^2$—Ar$^1$—CHO  II

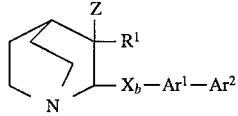  III

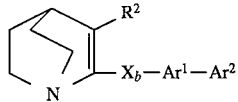  IV

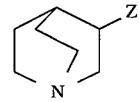  V

Ar$^2$—Ar$^1$—XH  VI

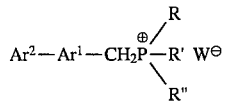  VII

Ar$^2$—Ar$^1$—M  VIII
Ar$^2$—Ar$^1$—CH$_2$—W  VIIa

We claim:
1. A compound of formula I,

Q—Ar$^1$—Ar$^2$  I or a pharmaceutically acceptable salt thereof, wherein:
Q is of formula Ib;

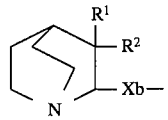  Ib

R$^1$ is selected from hydrogen, (1–6C)alkyl, halogeno and hydroxy; R$^2$ is selected from (1–6C)alkyl, halogeno and hydroxy; or R$^1$ and R$^2$ when taken together define an oxo group;

Xb is selected from —CH$_2$—, =CH— and —CH(OH);

Ar$^1$ is a 1,4-phenylene moiety;

Ar$^2$ is phenyl; and one or both of Ar$^1$ and Ar$^2$ is optionally unsubstituted or substituted by one or more substituents independently selected from halogeno, hydroxy, amino, nitro, cyano, carboxy, carbamoyl, (1–6C)alkyl, (2–6C)alkenyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno-(1–6C)alkyl and (1–6C)alkanoylamino;

provided that when one of R$^1$ and R$^2$ is hydroxy, the other of R$^1$ and R$^2$ is not hydroxy or halogeno; and provided that when R$^1$ and R$^2$ together define an oxo group and Xb is =CH—, then Ar$^1$ and Ar$^2$ phenyl rings are not both unsubstituted.

2. A compound as claimed in claim 1 wherein Q is of formula Ib; R$^1$ is selected from hydrogen, methyl, ethyl, propyl, isopropyl, butyl, iso-butyl, sec-butyl, fluoro, chloro, bromo, and hydroxy; R$^2$ is selected from methyl, ethyl, propyl, isopropyl, butyl, iso-butyl, sec-butyl, fluoro, chloro, bromo, and hydroxy; or R$^1$ and R$^2$ when taken together define an oxo group; Xb is selected from —CH$_2$—, =CH— and —CH(OH); Ar¹ is a 1,4-phenylene moiety; Ar² is phenyl; and wherein one or both of Ar¹ and Ar² is optionally unsubstituted or substituted by one or more substituents independently selected from fluoro, chloro, bromo, hydroxy, amino, nitro, cyano, carboxy, carbamoyl, methyl, ethyl, propyl, isopropyl, butyl, isobutyl, sec-butyl, allyl, but-2-enyl, 2-methyl-2-propenyl, methoxy, ethoxy, propoxy, isopropoxy, butoxy, methylamino, ethylamino, propylamino, butylamino, dimethylamino, diethylamino, methylpropylamino, dipropylamino, N-methycarbamoyl, N-ethylcarbamoyl, N-propylcarbamoyl, N,N-dimethylcarbamoyl, N,N-diethylcarbamoyl, methoxycarbonyl, ethoxycarbonyl, propoxycarbonyl, methylthio, ethylthio, propylthio, isopropylthio, butylthio, methylsulphinyl, ethylsulphinyl, propylsulphinyl, isopropylsulphinyl, butylsulphinyl, methylsulphonyl, ethylsulphonyl, propylsulphonyl, isopropylsulphonyl, butylsulphonyl, flurormethyl, difluoromethyl, trifluoromethyl, formamido, acetamido, propionamino, isopropionamido, butyramino, and iso-butyramino.

3. A method of treating a disease or medical condition mediated by the inhibition of squalene synthase by administering to a warm-blooded animal in need thereof a squalene synthase inhibiting amount of a compound of formula I,

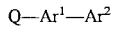  I or a pharmaceutically acceptable salt thereof, wherein:

Q is of formula Ib;

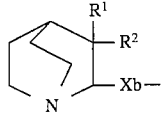  Ib $R^1$ is selected from hydrogen, (1–6C)alkyl, halogeno and hydroxy; $R^2$ is selected from (1–6C)alkyl, halogeno and hydroxy; or $R^1$ and $R^2$ when taken together define an oxo group;

Xb is selected from —CH$_2$—, =CH— and —CH(OH);

Ar¹ is a 1,4-phenylene moiety;

Ar² is phenyl; and one or both of Ar¹ and Ar² is optionally unsubstituted or substituted by one or more substituents independently selected from halogeno, hydroxy, amino, nitro, cyano, carboxy, carbamoyl, (1–6C)alkyl, (2–6C)alkenyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl, halogeno-(1–6C)alkyl and (1–6C)alkanoylamino;

provided that when one of $R^1$ and $R^2$ is hydroxy, the other of $R^1$ and $R^2$ is not hydroxy or halogeno.

4. A compound as claimed in claim 1, wherein $R^1$ is hydrogen or (1–6C)alkyl; $R^2$ is hydroxy or halogeno; or $R^1$ and $R^2$ together define an oxo group; and Xb is —CH$_2$— or —CH(OH)—.

5. A compound as claimed in claim 4 which is selected from:

2-(4-biphenylmethyl)-3-quinuclidinone; and 2-(4-biphenylmethyl)-3-quinuclidinol;

2-(4-biphenylmethyl)-3-methyl-3-quinuclidinol;

2-(1-hydroxybiphenyl-4ylmethyl)quinuclidin-3-ol;

and pharmaceutically acceptable salts thereof.

6. A pharmaceutical composition comprising a compound of formula I, or a pharmaceutically-acceptable salt thereof, as claimed in claim 1 together with a pharmaceutically acceptable diluent or carrier.

* * * * *